US007918899B2

(12) United States Patent
Girardot et al.

(10) Patent No.: US 7,918,899 B2
(45) Date of Patent: Apr. 5, 2011

(54) VARIABLY CROSSLINKED TISSUE

(75) Inventors: Jean-Marie Girardot, Dunwoody, GA (US); Marie-Nadia Girardot, Dunwoody, GA (US)

(73) Assignee: Biomedical Design, Inc., Dunwoody, GA (US)

( * ) Notice: Subject to any disclaimer, the term of this patent is extended or adjusted under 35 U.S.C. 154(b) by 668 days.

(21) Appl. No.: 11/276,398

(22) Filed: Feb. 27, 2006

(65) Prior Publication Data

US 2006/0159641 A1 Jul. 20, 2006

Related U.S. Application Data

(63) Continuation-in-part of application No. 10/892,924, filed on Jul. 16, 2004, which is a continuation of application No. PCT/US03/01757, filed on Jan. 21, 2003.

(60) Provisional application No. 60/351,996, filed on Jan. 25, 2002.

(51) Int. Cl.
*A61L 17/00* (2006.01)

(52) U.S. Cl. .......... 8/94.11; 623/2.1; 623/915; 623/918; 623/919

(58) Field of Classification Search .................. 8/94.11; 422/28; 424/422; 623/2.1, 915, 918, 919
See application file for complete search history.

(56) References Cited

U.S. PATENT DOCUMENTS

| 3,628,248 | A | 12/1971 | Kroder et al. |
| 4,082,507 | A | 4/1978 | Sawyer |
| 5,104,405 | A | 4/1992 | Nimni |
| 5,447,536 | A | 9/1995 | Girardot et al. |
| 5,509,932 | A | 4/1996 | Keogh et al. |
| 5,733,339 | A | 3/1998 | Girardot et al. |
| 5,911,951 | A | 6/1999 | Girardot et al. |
| 6,117,979 | A | 9/2000 | Hendriks et al. |
| 6,132,986 | A | 10/2000 | Pathak et al. |
| 6,166,184 | A | 12/2000 | Hendriks et al. |
| 6,506,339 | B1 | 1/2003 | Girardot et al. |
| 6,521,179 | B1 | 2/2003 | Girardot et al. |
| 7,053,051 | B2 | 5/2006 | Hendriks et al. |
| 7,060,103 | B2 | 6/2006 | Carr et al. |
| 2002/0095218 | A1 | 7/2002 | Carr et al. |
| 2004/0253291 | A1 | 12/2004 | Girardot et al. |
| 2005/0020506 | A1 | 1/2005 | Drapeau et al. |

FOREIGN PATENT DOCUMENTS

WO WO01/10209 * 2/2001

OTHER PUBLICATIONS

Hermanson, G.T., *Bioconjugate Techniques*, Academic Press 1996, Chapter 3, pp. 169-185.
Girardot, J.M. And Girardot, M.N., "Amide cross-linking: an alternative to glutaraldehyde fixation," J. Heart Valve Dis. 5(5):518-525 (1996).
Everaerts, F. et al., "Reduction of calcification of carbodiimide-processed heart valve tissue by prior blocking of amine groups with monoaldehydes," J. Heart Valve Dis. Mar. 2006;15(2):269-277.
PCT/US07/04653 Search Report dated Aug. 22, 2008.

* cited by examiner

*Primary Examiner* — Mark Kopec
*Assistant Examiner* — Haidung D Nguyen
(74) *Attorney, Agent, or Firm* — Fitch, Even, Tabin & Flannery

(57) ABSTRACT

Non-glutaraldehyde fixation of an organ or a prosthesis for implantation in a mammal is based upon carbodiimide treatment. A solution containing a sterilizing agent, such as EDC, in combination with a coupling enhancer, such as Sulfo-NHS, and a high concentration of a diamine cross linking agent is used. As a result, only minimal surface reduction occurs during fixation, and the resultant products show a dramatic increase in resistance to calcification.

31 Claims, 4 Drawing Sheets

# VARIABLY CROSSLINKED TISSUE

CROSS-REFERENCE

This application is a continuation-in-part application of Ser. No. 10/892,924, filed Jul. 16, 2004, to which application priority is claimed under 35 USC § 120, which is a continuation of PCT/US03/01757, filed on Jan. 21, 2003, which claims the benefit of priority of U.S. Provisional Application No. 60/351,996, filed Jan. 25, 2002; each priority application is incorporated herein by reference in its entirety.

FIELD OF THE INVENTION

This invention relates to a process for fixing human or animal tissue prior to implantation.

BACKGROUND OF THE INVENTION

Calcification of glutaraldehyde-preserved or "fixed" bioprosthetic heart valves frequently occurs and leads to failure due to stenosis and regurgitation. In addition, the slow release of glutaraldehyde from the implanted device is cytotoxic. Several methods of tissue cross linking or fixing that are independent of glutaraldehyde have been presented, and they include acyl azide, photooxidation, epoxy, genipin and carbodiimide. The latter is described in U.S. Pat. No. 5,733,339 issued Mar. 31, 1998. However, it is acknowledged that tissue shrinkage occurs during fixation, and no cross linking method has yet been perfected that totally avoids tissue shrinkage (J. Heart Valve Dis. 2001; 10(1): 111-124). While this may be of no particular concern with respect to pericardium or tissue for which tailoring will take place after fixation, it may well be an issue for porcine aortic root leaflets where precise interengagement, i.e. coaptation, is very important and excessive shrinkage may induce insufficient coaptation of the cusps which could render the valve incompetent. Therefore, the need for improved fixation technology that induces only minimum tissue shrinkage still exists, and the search for such technology has continued.

In addition to the problem of tissue shrinkage, it has also been found that various prosthetic devices require different degrees of cross linking. In general, cross linking provides the advantage of blocking or masking antigenic moieties within the protein structure of the prosthesis, thereby reducing or eliminating the body's immune response to the foreign object. Cross linking can also increase the durability of the prosthetic device by rendering the surface of the prosthesis resistant to biochemical degradation. Finally, cross linking can impart some rigidity to the prosthesis, which is often desirable for particular applications.

In contrast, a less highly cross linked tissue that is used as a prosthetic device will be expected to possess less structural rigidity, and thus to be more flexible. In addition, it would be expected that such tissues would be more likely to induce an immune response and to biodegrade over time. A tissue with little or no cross linking would be expected to exhibit properties similar to those of fresh tissue. It would be expected to be relatively fragile, flexible and susceptible to biodegradation. In addition, unless steps are taken to block antigenic sites that are normally blocked during the cross linking procedure, a non-cross linked tissue would also be expected to elicit immunological responses similar to those elicited by fresh tissue.

While fully cross linked tissue possesses many advantages, there are applications in which minimally cross linked tissue and partially cross linked tissue would make a superior implant. A partially cross linked tissue would be useful in applications where flexibility of the cross linked tissue is of primary importance. Thus, a minimally cross linked tissue would be useful in applications where maximum flexibility would be desirable; e.g. in subdermal reconstructive surgery, etc.

Thus, there is a need for a process of preparing a bioimplant in which the degree of cross linking can be varied from minimally to partially to fully cross linked. There is similarly a need for a such a process in which the partially and minimally cross linked tissues do not elicit an immune response. These and related needs are satisfied by embodiments of the present invention.

SUMMARY OF THE INVENTION

The foregoing and other needs are satisfied by embodiment of the present invention, which provide a method of making a sterilized and cross linked biological tissue. The method commences with treating a fresh biological tissue to produce a starting biological tissue. The starting biological tissue is characterized as being for preparation of a minimally cross linked (MX), partially cross linked (PX) or fully cross linked (FX) biological tissue. If the starting biological tissue is for preparation of partially or fully cross linked biological tissue, the initial treatment includes cross linking the tissue in the presence of a suitable cross linking agent under conditions suitable to obtain the desired degree of cross linking. If the starting biological tissue is for preparation of minimally cross linked biological tissue, the initial treatment does not include cross linking the tissue. The starting biological tissue is then subjected to one or more additional steps for sterilizing the starting biological tissue. If the starting biological tissue is for preparing minimally cross linked biological tissue or partially cross linked biological tissue, it is contacted with a blocking solution and a sterilization solution. If the starting biological tissue is for preparing fully cross linked biological tissue, it is contacted with at least a sterilization solution. The blocking solution contains at least a blocking agent and a sterilizing agent; and the sterilizing solution contains at least a sterilizing agent.

The foregoing and other needs are further satisfied by embodiments of the present invention, which provide a method of making a sterilized and variably cross linked biological tissue. The method comprises controlling the degree of cross linking of the biological tissue by first contacting a fresh biological tissue with a cross linking solution, a blocking solution, or first a cross linking solution and then a blocking solution. The degree of cross linking in the biological tissue is controlled by selecting conditions, such as contact time and/or temperature, and appropriate solutions, such as cross linking solution, blocking solution, or both, to which the fresh biological tissue is exposed during the step of preparing the starting biological tissue for producing fully, partially or minimally cross linked biological tissue. The process next comprises contacting the biological tissue with a sterilizing solution. The cross linking solution comprises a cross linking agent, a coupling agent, and a coupling enhancer. The blocking solution comprises a blocking agent and a sterilizing agent. The sterilizing solution comprises a sterilizing agent.

An improved fixation method based on water-soluble carbodiimide treatment has been found which results in tissue that is as effectively cross-linked as glutaraldehyde-fixed tissue, but that exhibits only minimal shrinkage as a result of fixation, and that exhibits surprisingly improved resistance to calcification after implantation in a mammal.

In a more particular aspect, the invention provides a process of fixing animal tissue to render it suitable for implantation in living mammals, which process comprises treating said animal tissue with an effective amount of a coupling agent which promotes the formation of amide bonds between reactive carboxyl moieties and reactive amino moieties, in combination with a coupling enhancer, and with a cross linking agent containing at least two reactive amine moieties, said diamine cross linking agent being present in an amount of at least about 80 millimolar, and said treatment being carried out in a manner which results in the formation of amidated links between said cross linking agent and reactive moieties carried by the molecules of said animal tissue, whereby said tissue is rendered resistant to protease digestion while incurring only minimal surface reduction during fixation and whereby the fixed tissue is highly resistant to calcification.

In another particular aspect, the invention provides a process of fixing fresh animal tissue to render it suitable for implantation in living mammals, which process comprises washing but not otherwise altering fresh tissue excised from a donor animal, treating said washed animal tissue with an effective amount of a cross linking agent containing at least two reactive amine moieties and with a coupling agent in combination with a coupling enhancer, which promotes the formation of amide bonds between reactive carboxyl moieties and reactive amino moieties, said diamine cross linking agent being present in an amount of at least about 80 millimolar, and said treatment being carried out in a manner which results in the formation of amidated links between said cross linking agent and reactive moieties carried by the molecules of said animal tissue, whereby said tissue is rendered resistant to protease digestion while incurring only minimal surface reduction during fixation and whereby the fixed tissue is highly resistant to calcification.

In a further particular aspect, the invention provides a prosthesis formed at least partially of animal tissue containing cross-links between and within the proteinaceous molecules of said tissue, which cross-links are comprised of amide bonds between reactive moieties on said tissue and additional amide bonds between reactive moieties on said tissue and diamine cross linking agents having a carbon chain length of at least 4 carbon atoms, said cross linking having been achieved by subjection of said tissue to an aqueous solution containing an effective amount of a water-soluble coupling agent which promotes the formation of amide bonds, a coupling enhancer and a concentration of between about 80 and about 130 millimolar of said diamine cross linking agent.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
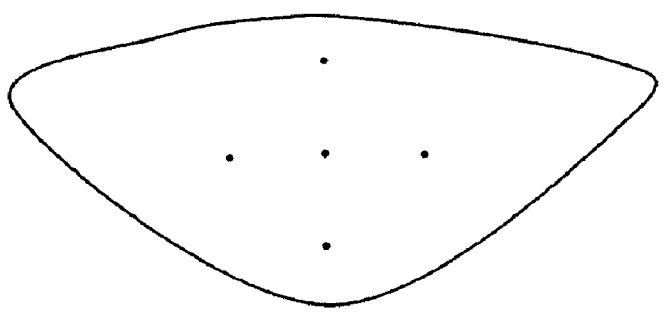
FIG. 1 is a drawing of a porcine aortic leaflet showing dots that indicate the marking that was carried out to measure the amount of surface reduction which occurs during fixing.

The basic fixation process with which the present invention is concerned is described in U.S. Pat. No. 5,733,339, the disclosure of which is incorporated herein by reference. It was surprisingly found that, by very substantially increasing the amount of diamine cross linking agent, dramatic effects can be achieved using the basic carbodiimide cross linking process.

It has also been found that a variably cross linked bioprosthetic tissue can be prepared in accordance with embodiments of the invention set forth herein.

As used herein, the term "bioprosthetic tissue" is meant to include any organ or tissue that is derived in whole or in part from a human or an animal, or which is produced from other organic tissue, and which is to be implanted, either by itself or as part of a bioprosthesis, in a human or in an animal. Thus, the term generally includes bioprosthetic tissue such as hearts, heart valves and other heart components, pericardium, vascular grafts, urinary tract and bladder components, tendons, ligaments, bowel, and soft tissues in general, such as skin, collagen and the like. Although the prosthetic tissue will very often be one which is made from natural tissues, including but not limited to human, porcine, equine, bovine, ovine, caprine, canine or feline tissue, other natural materials, well known to those having ordinary skill in this art, also can be used.

The one-step fixation method described herein consists of stabilizing the bioprosthetic tissue by binding reactive carboxyl moieties of the tissue either to a reactive amine moiety on the tissue or to a cross linking agent, in such a manner as to leave few active moieties on or within the tissue.

The term "cross linking", as used herein, refers to the fixation of bioprosthetic tissue that results from the formation of links of various lengths within and between the molecules of the tissue, such links resulting from amide bond formation either (a) between two reactive moieties of the tissue, thus forming short covalent links within and between the molecules of the tissue, or (b) between reactive moieties on the tissue and a covalently bound cross linking agent.

The term "cross linking agent" is used herein to describe a diamine having at least two free primary amine groups, preferably at each of its ends, which is capable of forming amide bonds with carboxyl groups on the proteinaceous animal tissue. It should preferably be a straight chain or a branched compound having from 4 to 12 carbon atoms; alternatively, but perhaps less desirably, carbocyclic compounds can be employed where the reactive amine moieties appropriately located on the ring, such as 2,4,6-triaminobenzene. More preferably, a di- or triamino cross linking agent is chosen which has a molecular weight of about 190 or less and preferably about 150 or less so as to assure adequate penetration into the fresh tissue usually being treated. Most preferably, it is a straight chain from 6 to 8 carbon atoms in length with one reactive amine located at each end. Although the cross linking agent may have optional substitutions along its length, it is preferably hydrocarbon that is substituted only with the reactive amines, e.g. a straight chain alkane having amines at each extremity. Preferred agents are 1,6-hexanediamine and 1,7-heptanediamine.

The terms "coupling agent" and "coupling enhancer", as used herein, refer to reagents that respectively promote and enhance the formation of amide bonds. These bonds may be formed between a reactive amine and a reactive carboxyl on the tissue (thus linking two such closely located reactive groups), or between a reactive amine on a cross linking agent and a reactive carboxyl on or within the tissue. Those of skill in the peptide synthesis and related art will be familiar with such reagents, e.g. water-soluble carbodiimides and succinimides.

The coupling agent used in the preferred embodiments is 1-ethyl-3(3-dimethylaminopropyl)carbodiimide hydrochloride (EDC), although other suitable coupling agents such as N-hydroxysuccinimide can also be used. The preferred coupling enhancer used in the embodiment where EDC is used as the coupling agent is N-hydroxysulfosuccinimide (Sulfo-NHS), although other suitable coupling enhancers, such as HOBt, DMAP and N-hydroxysuccinimide (NHS), can also be used. The concentration of the coupling agent and of the coupling enhancer can vary. However, appropriate concentrations are readily determinable by those of skill in the art. Preferably, the coupling agent is used in a concentration from about 1 mM to about 500 mM, more preferably at about 100 mM or less, and most preferably at between about 20 mM and 50 mM. The coupling enhancer is preferably employed at between 0.5 mM and about 50 mM and more preferably at about 10 mM or less.

The cross linking agents, the coupling agent and the coupling enhancer as well as their reaction products are preferably water-soluble. They should be selected such to maximize fixation and optimize cross linking of the tissue, while minimizing the risks of damage to the prosthetic tissue during the fixation process, and of toxicity, inflammation, calcification, etc, after implantation. All solutions used for cross linking are preferably filtered, before use, through 0.45 µm or less filters to minimize risks of contamination.

Reaction conditions for the cross linking of the prosthesis may vary, depending on the cross linking, coupling and enhancing agents employed. In general, the cross linking process is carried out in an aqueous buffer selected from among those well known to those of ordinary skill in this art as to provide the most efficacious cross linking reaction, while minimizing risks of calcification. Examples of suitable buffers include, but are not limited to, N-2-hydroxyethylpiperazine-N'-ethanesulfonic acid (HEPES) and 3-(N-morpholino)propanesulfonic acid (MOPS), and the like.

The pH and concentration of the buffered solution can vary, again depending upon the cross linking, coupling and enhancing agents employed. Preferably, the buffer concentration and pH are chosen to provide the most effective cross linking reaction while being the least harmful to the prosthesis. For example, with EDC as the coupling agent and Sulfo-NHS as the coupling enhancer, the pH of the treatment solution is maintained at between about 5.0 to about 7.4. The reaction temperature may be between about 40° C. and 0° C.; preferably, the reaction is simply carried out at room temperature, e.g. between about 18 and 25° C.

Typically, the fresh prosthetic tissue to be fixed by the one-step cross linking method of the present invention is kept on ice until it can be rinsed several times in ice-cold 0.85% saline or some other suitable solution. Such washing or rinsing is preferably carried out immediately after being excised from the donor mammal, but in any event within 48 hours thereafter. If additional storage time is needed, the rinsed tissue is then stored, but preferably not longer than for 24 hours, in an appropriate buffer at a low temperature, such as about 4° C. No other pretreatment is required, nor is any desired that would alter the properties of such fresh tissue.

One Step Process

The surprising improvement in properties of the resultant fixed bioprosthetic device has been found to result from the use of a very large excess of the specified diamine cross linking agent over and above the amount needed to effectively fix the bioprosthetic tissue. It has been surprisingly found that when about 4 to 5 times as much diamine cross linking agent is used, compared to the highest amount mentioned in the '339 patent, to treat otherwise untreated (except for washing) fresh tissue, significant improvements result without any detrimental change in other advantageous properties of the resultant product. More specifically, the reduction in the surface area occurring during fixation, referred to hereinafter as Surface Reduction, is decreased by more than 50%, and the resistance of the product to calcification is dramatically increased. These advantages are obtained without any disadvantageous change in thermal denaturation, resistance to protease digestion or resistance to collagenase digestion.

The concentration of the diamine cross linking agent is preferably between about 80 and about 135 millimolar, more preferably between about 90 and 130 millimolar, still more preferably between about 95 and 125 millimolar, and most preferably between about 100 and 125 millimolar. As previously indicated, the preferred diamine cross linking agent has a carbon chain length not greater than 12 carbon atoms, e.g. between 4 and 8 carbon atoms, more preferably is a straight chain alkane having amine groups at its respective ends, and most preferably is 1,6-hexanediamine. Treatment of the animal tissue is preferably carried out by application of an aqueous solution containing the coupling agent, the coupling enhancer and the cross linking diamine. The concentrations of the water-soluble coupling agent, preferably EDC, and the coupling enhancer, preferably Sulfo-NHS, are as previously discussed, namely between about 10 mM and about 100 mM of EDC and between about 0.5 mM and about 10 mM of Sulfo-NHS.

It is of course well known that before a bioprosthetic device can be implanted in a mammal, primarily a human, sterilization must be effected, and such is normally done during the packaging step. Accordingly, it is often important that tissue which advantageously suffered only minimal surface reduction during fixation does not thereafter shrink during sterilization. This is of course of particular importance for the treatment of replacement heart valves or the like where coaptation may be adversely affected (as opposed to raw materials that will be subsequently tailored into valves or other bioprosthetic devices). Particularly effective sterilization processes for bioprosthetic material are described in U.S. Pat. Nos. 5,911,951, 6,506,339 and 6,521,179, which are incorporated herein by reference in their entirety. It has been shown that bioprosthetic materials, when subjected to fixation followed by sterilization for 48 hours at 40° C. in an aqueous solution of 25 mM EDC, still show only minimal surface reduction, and this remains true even if such sterilization is repeated 3 times. Such testing by employing repetition of the sterilization procedure is merely precautionary; on occasion, when bioprosthetic devices are being sterilized, if a target indicator that is included with the batch still shows positive, for whatever reason, at the end of the procedure, it may be necessary to repeat the sterilization procedure and, on rare occasions, even repeat it twice. Accordingly, it was felt prudent to measure surface reduction for tissue that had been subjected to such somewhat extreme conditions. It was also found that no significant shrinkage would occur when sterilization was carried out under treatment with a solution containing 20% isopropanol and 80% water that is 25 mM EDC and 100 mM of ethanolamine (a blocker) for 48 hours at 40° C.

Variably Cross Linked Tissue

The foregoing and other needs are satisfied by embodiment of the present invention, which provide a method of making a sterilized and cross linked biological tissue. The method commences with treating a fresh biological tissue to produce a starting biological tissue. The starting biological tissue is characterized as being for preparation of a minimally cross linked (MX), partially cross linked (PX) or fully cross linked (FX) biological tissue. If the starting biological tissue is for preparation of partially or fully cross linked biological tissue, the initial treatment includes cross linking the tissue in the presence of a suitable cross linking agent under conditions suitable to obtain the desired degree of cross linking. If the starting biological tissue is for preparation of minimally cross linked biological tissue, the initial treatment does not include cross linking the tissue. The starting biological tissue is then subjected to one or more additional steps for sterilizing the starting biological tissue. If the starting biological tissue is for preparing minimally cross linked biological tissue or partially cross linked biological tissue, it is contacted with a blocking solution and a sterilization solution. The blocking solution contains at least a blocking agent and a sterilizing agent; and the sterilizing solution contains at least a sterilizing agent. If the starting biological tissue is for preparing fully cross linked biological tissue, it is contacted with at least a sterilization solution.

The variable cross linking method of the present invention can be envisioned as comprising a treatment procedure and a sterilization procedure. The treatment procedure produces a starting biological tissue for preparing minimally, partially or fully cross linked biological tissue. The sterilization procedure sterilizes the starting biological tissue to produce the minimally, partially or fully cross linked biological tissue as a final product.

In the context of this invention, the terms "treatment," "treating," "to treat" and related verb conjugates, when applied to fresh biological tissue, refer to one or more measures taken to prepare the fresh tissue to produce a starting biological tissue. The starting biological tissue thus treated is classified as starting biological tissue for preparing minimally cross linked, partially cross linked or fully cross linked biological tissue.

In some embodiments, treatment includes cleaning the fresh biological tissue, e.g. by rinsing it with a saline or buffer solution and/or shaving it to remove excess fat. In some embodiments, treatment includes cutting the biological tissue into properly sized and shaped pieces, and/or weighing the pieces. Thus, all fresh biological tissues, whether they are to be minimally, partially or fully cross linked, are treated in some way before they are sterilized.

In accordance with the present invention, treating fresh biological tissue is carried out under conditions suitable to control the degree of cross linking of the biological tissue. Controlling cross linking entails subjecting biological tissue to conditions that are suitable for preparing a starting biological tissue for preparing minimally cross linked, partially cross linked or fully cross linked biological tissue. Controlling cross linking includes determining to what degree the biological tissue is to be cross linked and, if necessary, contacting the biological tissue with an appropriate cross linking solution. Thus, "controlling cross linking" means adjusting conditions, such as reagents, reagent concentrations, reaction times and temperatures, to obtain a suitable starting biological tissue. Thus, "controlling cross linking" embraces preventing cross linking, minimizing cross linking, maximizing cross linking or controlling cross linking along a continuum between minimal and maximal cross linking.

In other particular embodiments, the starting biological tissue is for producing a minimally cross linked biological tissue. In some such cases, controlling cross linking requires that the biological tissue not be contacted with a cross linking solution prior to sterilization. In other embodiments where the starting biological tissue is for producing a minimally cross linked biological tissue, the starting biological tissue may be contacted with a cross linking solution under conditions (e.g. short period of time, low temperature, low concentration of cross linking agent, coupling agent and/or coupling enhancer), such that the resulting degree of cross linking is negligible.

In some particular embodiments, controlling cross linking of biological tissue results in production of a starting biological tissue for preparing partially cross linked or fully cross linked biological tissue. In embodiments where the starting biological tissue is for producing a partially or fully cross linked biological tissue, controlling cross linking means selecting conditions for cross linking the biological tissue and subjecting the fresh biological tissue to such conditions to produce the starting biological tissue for preparing partially or fully cross linked biological tissue. The conditions to be selected include: concentration of cross linking agent, concentration of coupling agent, concentration of coupling enhancer, temperature or the reaction and time of reaction.

A "starting biological tissue" is a tissue that has been treated in some way, as defined above, but has not been subjected to at least one sterilization step. Starting biological tissues include starting biological tissues for preparing minimally cross linked biological tissues, starting biological tissues for preparing partially cross linked biological tissues, and starting biological tissues for preparing fully cross linked biological tissues.

The sterilization steps, described in more detail in the examples, include contacting the biological tissue with one or more solutions containing a sterilizing agent. One such solution is referred to herein as a "blocking solution," as it contains both a sterilizing agent and a blocking agent. Another such solution is referred to as a "sterilizing solution," as it contains sterilizing agent but need not contain a blocking agent. In some embodiments, the sterilizing solution contains no blocking agent.

The degree of cross linking in a cross linked biological tissue can be characterized as minimally, partially or fully cross linked. The degree of cross linking can be measured by several methods that measure characteristics of the biological tissue that correlate with the degree of cross linking. In one such method, the temperature at which the biological tissue begins to shrink is measured. In general, the greater the cross linking, the greater the shrinkage temperature, as a more highly cross linked tissue will resist thermal denaturation and thus resist shrinkage at lower temperatures, only succumbing to denaturation at higher temperatures. The heat shrinkage method is explained in more detail in Example 5.

In another such method of measuring cross linking, the ability of the biological tissue to resist digestion by a proteolytic enzyme, such as collagenase or pronase, is measured. In general, a tissue that is cross linked to a greater degree will resist protease digestion to a greater degree than will a tissue cross linked to a lesser degree. This method is explained in more detail in Example 5.

The term minimally cross linked (MX) refers to a biological tissue that has substantially no cross linking between molecules in the biological tissue, other than insubstantial zero-length bonds between adjacent carboxyl and amine moieties of the collagen molecules. Minimal cross linking can be measured and verified by various methods known in the art. In some embodiments, a minimally cross linked tissue has a shrinkage temperature that is within about ±2° C. of corresponding fresh biological tissue. For example, porcine aortic leaflets that are minimally cross linked have a shrinkage temperature of about 68° C.

Additionally, minimal cross linking can be measured and verified by the pronase digestion method described in detail in Example 5. Minimally cross linked biological tissue resists protease digestion to a lesser degree than does partially cross linked (PX) or fully cross linked (FX) tissue. Thus, the percent tissue remaining after pronase digestion for minimally cross linked tissue is similar to that of fresh biological tissue. In general, fresh tissue is not resistant to protease digestion, nor is minimally cross linked tissue. In some embodiments, treatment of minimally cross linked biological tissue with pronase at 1 mg/ml for 24 hours results in % tissue remaining of about 0 to about 30% tissue remaining. In particular embodiments, the amount of tissue remaining is about 26%.

Full cross linking can be measured and verified by various methods known in the art. For example, in some embodiments, a fully cross linked tissue has a shrinkage temperature that is at least about 10° C. above that of fresh or minimally cross linked tissue. For example, porcine aortic leaflets that are fully cross linked have a shrinkage temperature of about 80° C., which is about 12° C. above that of the corresponding minimally cross linked tissue.

Full cross linking can be measured and verified by the pronase digestion method described in detail in Example 5. Fully cross linked biological tissue will resist pronase digestion to a greater degree than will partially cross linked (PX) or minimally cross linked (MX) tissue. Thus, the percent tissue remaining after pronase digestion for fully cross linked tissue is much greater than that of fresh biological tissue. In general, fully cross linked tissue is very resistant to protease digestion. In some embodiments, treatment of fully cross linked tissue with pronase at 1 mg/ml for 24 hours results in % tissue remaining of at least about 80% tissue remaining. In particular embodiments, the amount of tissue remaining is about 88%.

The term partially cross linked (PX) refers to a biological tissue that has been cross linked to a degree intermediate between MX and FX. In some embodiments, partial cross linking can be established by measuring one or more characteristics of a cross linked biological tissue and comparing them to the corresponding characteristics in a fully cross linked biological tissue and a minimally cross linked biological tissue. Characteristics of cross linked tissue include shrinkage temperature and resistance to protease digestion, as described above and in Example 5. In some embodiments, a partially cross linked tissue is a cross linked tissue in which at least one characteristic of the cross linked tissue is greater than the corresponding characteristic (e.g. % tissue remaining after protease digestion or shrink temperature) for minimally cross linked tissue, and is less than the corresponding characteristic for fully cross linked tissue.

Partial cross linking can be measured and verified by various methods known in the art. For example, in some embodiments, a partially cross linked tissue has a shrinkage temperature that is at least about 4° C. above that of fresh or minimally cross linked tissue, but at least about 6° below that of fully cross linked tissue. For example, porcine aortic leaflets that are partially cross linked have a shrinkage temperature of about 73° C., which is about 5° C. above that of the corresponding minimally cross linked tissue and about 7° C. below that of the corresponding fully cross linked tissue.

Partial cross linking can be measured and verified by the pronase digestion method described in detail in Example 5. Partially cross linked biological tissue resists pronase digestion to a greater degree than does minimally cross linked (MX), but to a lesser degree than does fully cross linked (FX) tissue. Thus, the percent tissue remaining after pronase digestion for partially cross linked tissue is somewhat greater than that of fresh biological tissue, but not so great as for fully cross linked tissue. In some embodiments, treatment of partially cross linked tissue with pronase at 1 mg/ml for 24 hours results in % tissue remaining of greater than 50%, but less than 80% tissue remaining. In particular embodiments, the amount of tissue remaining is about 72%.

In some embodiments, the method of the invention can be envisioned as three separate processes. The MX process comprises providing fresh tissue, contacting the fresh tissue with a blocking solution and then contacting the tissue with a final sterilization solution to yield the final sterilized and minimally cross linked tissue. In some particular embodiments, the MX process also includes contacting the fresh tissue with a cross linking solution for a very short period of time and/or with very low concentrations of cross-linking reagents, such that substantially no cross linking takes place. The PX process entails contacting a fresh tissue with a low concentration of coupling agent and a low concentration of coupling enhancer in a buffer solution containing a cross linking agent, after which the tissue is contacted with the blocking solution and then the final sterilization solution to yield the PX tissue. The FX process entails contacting a fresh tissue with a buffered solution containing a higher concentration of coupling agent, a higher concentration of coupling enhancer in the presence of a cross linking agent to produce a cross linked tissue. The cross linked tissue is contacted with a final sterilization solution to produce the FX tissue. In some embodiments, the cross linked tissue may be contacted with a blocking solution between the cross linking and final sterilization steps.

The foregoing and other needs are further met by embodiments of the invention, which provide a method of making a sterilized and variably cross linked biological tissue. The method comprises optionally contacting a starting biological tissue selected from the group consisting of a fresh biological tissue and a cross linked biological tissue with a first sterilizing solution comprising a first sterilizing agent and a blocking agent to produce an intermediate biological tissue; and contacting the intermediate biological tissue with a second sterilizing solution comprising a second sterilizing agent to produce a sterilized and variably cross linked biological tissue.

The foregoing and other needs are met by embodiments of the invention, which provide a process of variably cross linking a starting biological tissue to produce a sterilized and cross linked biological tissue that is cross linked to a predetermined degree, either minimally, partially or fully. The process comprises selecting a starting biological tissue to be processed and selecting a degree of cross linking to be imparted to the starting biological tissue. The tissue is treated to prepare a starting biological tissue. Such treatment optionally includes contacting the fresh biological tissue with a cross linking solution to prepare a starting biological tissue for use in making a fully or partially cross linked biological tissue. The starting biological tissue is then contacted with at least one sterilizing solution. In the case of starting biological tissue for making minimally or partially cross linked biological tissue, the starting biological tissue is first contacted with a blocking solution and then with a sterilizing solution; in the case of starting biological tissue for making fully cross linked tissue, the starting biological tissue is contacted with at least a sterilizing solution. The blocking solution comprises sterilizing agent, blocking agent and optionally a penetration enhancer. The sterilization solution comprises a sterilization agent, a buffer and optionally a penetration enhancer.

Figure 5:
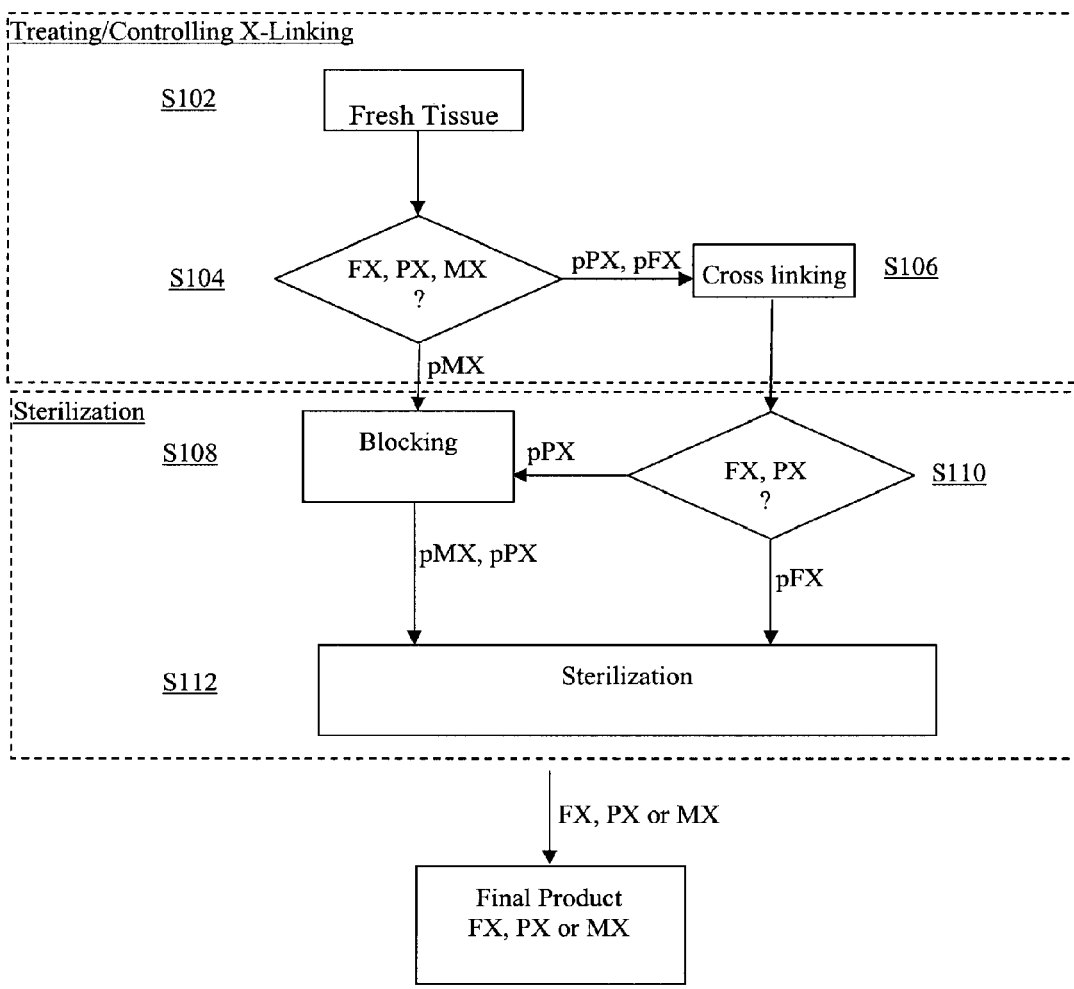
FIG. 5 is a flow chart schematically depicting an embodiment of the process according to the present invention.

The process can be further envisioned with reference to FIG. 5, which provides a flow diagram of the process according to the invention. The process can be envisioned as combining two sub-processes: treatment/controlling cross linking (S102, S104 and S106) and sterilization (S108, S110 and S112). More specifically, in a treatment step S102, fresh tissue from a suitable source, such as a slaughterhouse, is obtained, trimmed of fat, cut and rinsed with ice cold saline. Then, in S104, cross linking is controlled by determining whether the starting biological tissue will be for preparing minimally cross linked (MX), partially cross linked (PX), or fully cross linked (FX) biological tissue. If the starting biological tissue will be for preparing PX or FX tissue, the tissue (identified as pPX or pFX, the "p" indicating that it is in process) is subjected to a cross linking step S106, wherein the tissue is contacted with a cross linking solution containing a cross linking agent (e.g. an alkane diamine, such as 1,6-hexanediamine or 1,7-heptanediamine), a coupling agent (e.g. a carbodiimide, such as EDC), a coupling enhancer (e.g. N-hydroxysuccinimide (NHS) or Sulfo-N-hydroxysuccinimide (Sulfo-NHS)), and optionally a penetration enhancer (e.g. a $C_1$-$C_8$ alkanol, such as methanol, ethanol, propanol, isopropanol, butanol, pentanol, hexanol, heptanol or octanol). Cross linking is controlled by varying the concentration of cross linking agent, the concentration of coupling agent, the concentration of coupling enhancer, the concentration of penetration enhancer, the pH, the temperature and/or reaction time to produce a starting biological tissue having a particular degree of non-zero length cross linking. In the case of starting biological tissue for preparation of minimally cross linked biological tissue, the cross linking is controlled essentially by skipping cross linking (as shown for the embodiment diagramed in FIG. 5) or by reducing the concentration of cross linking agent, the concentration of coupling agent, the concentration of coupling enhancer, the concentration of penetration enhancer, the temperature and/or reaction time to such a degree that no or substantially no cross linking occurs in the biological tissue.

The amount of cross linking agent in the cross linking solution can be at least about 1 millimolar (mM), especially at least about 5 mM, e.g. in a range of about 1 to 500 mM, e.g. about 5 mM to about 130 mM, depending upon the amount of cross linking desired.

In general, it is considered advantageous to add a suitable buffer to the cross linking solution. The pH of the final solution should be in the range of about 5.0 to 7.4, especially about 6.5, and may be adjusted into that range by adding either acid or base as needed to achieve the target pH.

The amount of coupling agent can be at least about 0.1 mM, especially at least about 1.0 mM, e.g. from about 0.1 to 100 mM, especially about 1 to about 50 mM. Suitable coupling agents include carbodiimides, of which one example is EDC.

The amount of coupling enhancer can be at least about 0.01 mM, especially from about 0.05 to about 10 mM, e.g. from about 0.05 to about 5 mM, depending upon the degree of cross linking desired.

The amount of cross linking agent, coupling agent and coupling enhancer may each be independently varied to vary the degree of cross linking obtained in the biological tissue. As a purely illustrative, non-limiting example, a starting biological tissue for preparing fully cross linked (pFX) tissue may be prepared by using a cross linking solution comprising at least about 5 mM, e.g. approximately 10 to 30 mM of coupling agent (e.g. a carbodiimide like EDC), and at least about 0.1 mM, e.g. about 0.5 to 3 mM of coupling enhancer (e.g. NHS or S—NHS). In particular embodiments, a starting biological tissue for preparing a fully cross linked (FX) tissue may be prepared using about 15 to about 20 mM, especially about 20 mM, coupling agent and about 0.5 to 1.5 mM, especially about 1 mM coupling enhancer. Exemplary cross linking solution contact times for making a starting biological tissue for preparing a fully cross linked biological tissue are from about 1 hr to about 96 hr, from about 2 hr to about 72 hr, from about 4 hr to about 48 hr, or from about 8 hr to about 24 hr. Exemplary temperatures for making a starting biological tissue for preparing a fully cross linked biological tissue are from about 10° C. to about 50° C., from about 15° C. to about 45° C., or from about 20° C. to about 50° C.

As another purely illustrative, non-limiting example, a starting biological tissue for preparing partially cross linked (pPX) tissue can be prepared by contacting cleaned, fresh biological tissue with a cross linking solution comprising about 1 to about 5 mM, especially about 2.5 mM, coupling agent and about 0.05 to about 0.4 mM, especially about 0.125 mM coupling enhancer. Exemplary cross linking solution contact times for making a starting biological tissue for preparing a partially cross linked biological tissue are from about 1 hr to about 96 hr, from about 2 hr to about 72 hr, from about 4 hr to about 48 hr, or from about 8 hr to about 24 hr. Exemplary temperatures for making a starting biological tissue for preparing a partially cross linked biological tissue are from about 10° C. to about 50° C., from about 15° C. to about 45° C., or from about 20° C. to about 50° C.

In decision step S110, it is decided whether the tissue will be subjected to a blocking step S108. In the intermediate sterilization step S108, the starting biological tissue (pPX or pMX) is contacted with a blocking solution containing a blocking agent, a sterilizing agent and optionally a penetration enhancer. The blocking agent is a mono-functional reactive moiety capable of forming a stable covalent bond with a free carboxyl group in the proteins of the biological tissue, thereby blocking cross linking of the tissue. Although referred to herein as a "blocking solution," the person skilled in the art will recognize that, in addition to blocking some reactive sites on the tissue surface, the "blocking solution" also serves to sterilize the biological tissue.

As an illustrative, non-limiting example, the blocking agent may be a primary monamine that reacts with free carboxyl groups in the proteins making up the tissue. The purpose of the blocking agent is to prevent formation of zero length cross linking in tissues that are to be minimally or partially cross linked. The monamine can be a soluble primary monamine, and may contain one or more solubilizing functional groups, such as a hydroxyl group. A particularly suitable monamine for such applications is ethanolamine, which is advantageously prepared in a TRIS buffer solution. Other suitable monamines include propanolamine. The concentration of blocking agent can vary from about 10 to about 500 mM, especially about 50 to about 250 mM, and particularly about 100 mM of monamine blocking agent, e.g. ethanolamine, propanolamine or butanolamine. A particularly suitable blocking agent is about 100 mM of ethanolamine.

The amount of sterilizing agent, such as a carbodiimide (e.g. EDC) used in the blocking step S108 can vary from about 10 to about 30 mM, especially from about 20-25 mM in the presence of about 5-25% (vol-vol), especially about 20% of a suitable penetration enhancer, such as a C1-C8 alkanol, e.g. isopropanol or n-propanol.

In general, it is not necessary for a starting biological tissue for preparing a fully cross linked tissue to be subjected to a blocking step S108, as the a starting biological tissue for preparing fully cross linked tissue is generally fully cross linked in the cross linking step S106. As the reactive groups that would normally react with the coupling agent in the sterilization step 108 are generally fully blocked during the treatment/controlling cross linking step for preparing a starting biological tissue for preparing fully cross linked biological tissue, the blocking step S108 may be skipped for the pFX tissue, as is illustrated in FIG. 5. However, in an alternative embodiment, the pFX tissue may be subjected to the blocking step S108, in which case the addition of blocking agent is not considered to be detrimental to the overall processing of the FX tissue, and the additional sterilization step can only increase the sterility of the final product. As in the case of treating/controlling cross linking in the pMX tissue, the amount of time that the pFX tissue is contacted with blocking solution can be reduced as compared to that used for pMX or pPX tissue. In particular embodiments, the amount of time that the pFX tissue is contacted with blocking solution is less than 10%, less than 5%, less than 2% or less than 1% of that used for pMX or pPX tissue.

The pMX, pPX of pFX tissue is next subjected to a final sterilization step S112. In cases where the pFX tissue is not subjected to the blocking step S108, it passes directly from the decision step S110 to the final sterilization step S112. In any case, the final sterilization step S112 comprises contacting the pMX, pPX or pFX tissue with a sterilizing solution containing a sterilizing agent (e.g. a carbodiimide such as EDC), a buffer and optionally a penetration enhancer. The concentration of the sterilizing agent can be at least about 5 mM, e.g. from about 5 to about 50 mM, when used in the presence of a about 5-25% (vol-vol), especially about 20% (vol-vol), of a suitable penetration enhancer, such as a C1-C8 alkanol (e.g. isopropanol or n-propanol).

Although a buffer is recited in the foregoing paragraphs with reference to FIG. 5, it is to be understood that in some alternative embodiments of the process illustrated in FIG. 5, the process can be carried out without a buffer. Thus, in some embodiments of the invention, the process illustrated in FIG. 5 can be carried out with: a cross linking solution comprising a cross linking agent, a coupling agent and a coupling enhancer; a blocking solution comprising a sterilizing agent and a blocking agent; and a sterilizing solution comprising a sterilizing agent. In other embodiments of the invention, the process illustrated in FIG. 5 can be carried out with: a cross linking solution comprising a buffer, a cross linking agent, a coupling agent and a coupling enhancer; a blocking solution comprising a buffer, a sterilizing agent and a blocking agent; and a sterilizing solution comprising a buffer and a sterilizing agent. In still further embodiments of the invention, the process illustrated in FIG. 5 can be carried out with: a cross linking solution comprising a buffer, a cross linking agent, a coupling agent and a coupling enhancer; a blocking solution comprising a buffer, a penetration enhancer, a sterilizing agent and a blocking agent; and a sterilizing solution comprising a penetration enhancer, a buffer and a sterilizing agent.

Figure 6:
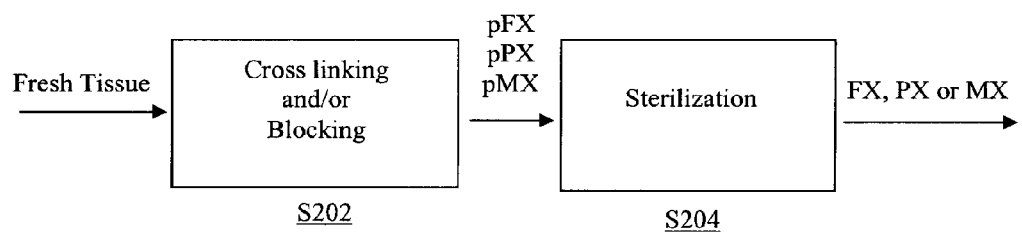
FIG. 6 is a flow chart schematically depicting an embodiment of the process of the present invention.

Thus, another way of conceptualizing the invention is as a two part process as shown in FIG. 6. In the first part of the process S202, a fresh biological tissue is cross linked, blocked or both. In S202 in FIG. 6, the degree of cross linking in the biological tissue is controlled by selecting conditions, such as whether the tissue will be contacted with a cross linking solution, a blocking solution, or both a cross linking solution and a blocking solution, the concentrations of reagents in the cross linking and/or blocking solutions, the temperature at which said contacting takes place, and the amount of time for which said contacting takes place. Suitable concentrations of cross linking agent, coupling agent, coupling enhancer, blocking agent and sterilizing agent, and suitable temperatures and reaction times, are discussed in more detail above. The resulting variably crosslinked biological tissue (pMX, pPX or pFX) is then subjected to a sterilization step S204.

The sterilization step 204 comprises contacting the biological tissue (pMX, pPX or pFX) with a sterilizing solution. The sterilizing solution comprises a sterilizing agent; and particular sterilizing agents, concentrations thereof, as well as times and temperatures for sterilization, are discussed in more detail above. The resulting sterilized and cross linked biological tissue (MX, PX or FX) is sterilized and variably cross linked biological tissue of the invention.

Example 5 sets forth a procedure for preparing variably cross linked tissues according to the invention. It should be understood that these examples do not place limits upon the scope of the invention as the metes and bounds of the invention are set forth in the claims appended hereto.

EXAMPLE 1

This first experiment was carried out to show the effect of 1-6 hexane diamine concentration on surface reduction during cross linking.

Eighty leaflets were excised from fresh porcine aortic roots. Each leaflet was blotted to remove excess buffer and placed flat, outflow side down, on a glass surface. Under a dissection microscope equipped with a reticule, the cusps were then marked in the radial and circumferential directions as shown in FIG. 1, with tissue marking dye following the manufacturer's recommendations. The distance between the center dot and each of the four exterior dots was 5 mm before cross linking; therefore, the maximum distance between markers was 10 mm. The leaflets were then randomly distributed in 4 groups of 20 cusps each and cross-linked by incubation under the following conditions:

Group 1. Aqueous solution of 11.25 mM 1,6-hexanediamine (DIA) in 20 mM HEPES buffer, pH 6.5, containing 20 mM 1-Ethyl-3-(3-Dimethylaminopropy-1)-Carbodiimide (EDC) and 1 mM N-hydroxysulfosuccinimide (Sulfo-NHS) for 96 hours at room temperature.

Group 2: Same as Group 1 but used 62 mM DIA.

Group 3: Same as Group 1 but used 112.5 mM DIA.

Group 4: The leaflets were incubated in a two step procedure according to the '339 patent. The first step was identical to Group 1 for 48 hours, and it was followed by a second step incubation with 7.5 mM suberic acid in the presence of 20 mM EDC/1 mM Sulfo-NHS.

After cross linking was completed, the distances between the markers were again measured using a microscope equipped with a reticule for the radial and circumferential direction to calculate surface reduction. Calibration of the microscope was performed before each use. Size reduction was calculated, and the results are presented in Table 1.

TABLE 1

| Group Number/ Conditions | Surface Reduction % of original (Mean ± SEM) |
|---|---|
| 1. DIA = 11.25 mM | 8.00 ± 0.9 |
| 2. DIA = 62 mM | 6.60 ± 1.3 |
| 3. DIA = 112.5 mM | 2.73 ± 0.81 |
| 4. DIA = 11.25 mM SUA = 7.5 mM | 12.2 ± 0.9 |

In this experiment, the two-step fixation samples, i.e. Group 4, showed a 12% reduction in surface area as compared to only about 3% for Group 3. In an experiment using comparable conditions, the shrinkage of glutaraldehyde-fixed leaflets was found to be 5% and higher. The results demonstrate that a significant reduction in leaflet shrinkage is obtained with increased DIA concentration, a result which is superior to glutaraldehyde fixation that has been the industry standard for at least two decades.

EXAMPLE 2

The following experiment was carried out to determine the effect of DIA concentration greater than 112.5 mM in cross linking.

Twenty-one leaflets for each condition were excised from fresh porcine aortic roots. For each condition, seven roots plus their 3 respective excised leaflets were incubated for 96 hours at room temperature in 250 ml of an aqueous solution of 20 mM HEPES and either 112.5 mM or 160 mM DIA, in the presence of 20 mM EDC and 1 mM Sulfo-NHS. After incubation, the samples were washed with sterile saline and then sterilized 3 times for 48 hours at 4° C. with 25 mM EDC in the absence (0%) of, or in the presence of either 5% or 20% isopropyl alcohol. For one condition, 100 mM ethanolamine was added as a blocker during sterilization with a solution containing 20% isopropanol.

The results are presented in Table 2 and demonstrate that 3 consecutive sterilization treatments of the leaflets fixed with 112.5 mM DIA, in the absence of isopropyl alcohol, do not induce significant shrinkage of the tissue, i.e. as compared to Table 1 for 112.5 mM DIA. Sterilization with the addition of either 5 or 20% alcohol does result in some shrinkage; however, addition of 100 mM ethanolamine when sterilization is being carried out in the presence of 20% isopropyl alcohol (when shrinkage would otherwise be the greatest) significantly inhibits such shrinkage from repeated sterilization. The data also indicate that increasing DIA concentration to 160 mM during the cross linking step induced 14% tissue shrinkage that remained (which was unaffected during sterilization in the absence or presence of isopropyl alcohol); this is an amount of shrinkage far greater than that resulting from standard fixing treatments.

TABLE 2

| DIA mM | Isopropyl Alcohol % | Surface Reduction % of original (Mean ± SEM) |
|---|---|---|
| 112.5 mM | 0 | 3.3 ± 1.3 |
| 112.5 mM | 5 | 6.7 ± 1.2 |
| 112.5 mM | 20 | 8.3 ± 1.4 |
| 112.5 mM | 20 + "blocker" | 4.3 ± 1.3 |
| 160 mM | 0 | 14.6 ± 1.3 |
| 160 mM | 5 | 14.0 ± 1.4 |
| 160 mM | 20 | 14.2 ± 1.3 |

EXAMPLE 3

The next experiment was carried out to determine the effect of the duration of incubation on cross linking of porcine aortic valves from three different standpoints.

Five groups of 4 valves each were incubated in an aqueous solution containing 20 mM HEPES, 112.5 mM DIA, pH 6.5, 20 mM EDC and 1 mM Sulfo-NHS for 3, 6, 24, 48 and 96 hours. The valves were then washed with sterile saline to eliminate any reaction byproducts. They were stored in 10 mM HEPES, 0.85% sodium chloride, pH 7.4, and 20% isopropyl alcohol until use. Thermal denaturation tests and tests for resistance to proteolytic degradation by collagenase and by protease were performed for the determination of cross linking efficacy. These test procedures are described in the J. Heart Valve Dis. 1996; 5(5):518-25. Fresh porcine aortic roots were used as a control.

a. Thermal Denaturation

Figure 2:
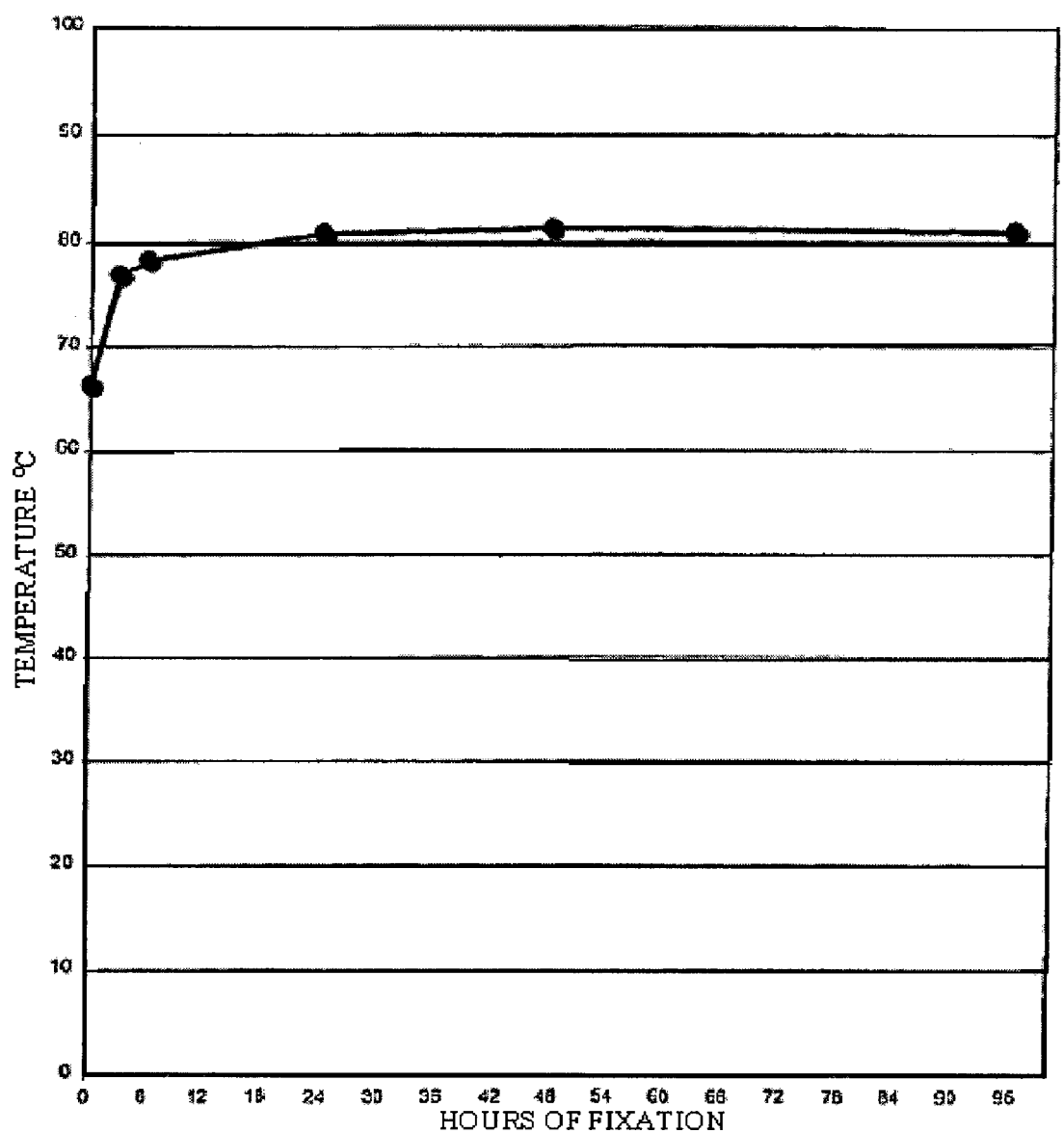
FIG. 2 is a graph which shows the effect of duration of fixation upon the thermal denaturation of porcine leaflets.

The leaflets were excised from the aortic roots and submitted (n=3 per condition) to thermal stability testing as described in the above reference. The results are shown in FIG. 2 and indicate that cross linking of the cusp tissue occurs reasonably rapidly with maximum stability to thermal denaturation being achieved at about 24 hours of incubation, with little change occurring thereafter.

b. Resistance to Digestion by Protease.

Figure 3:
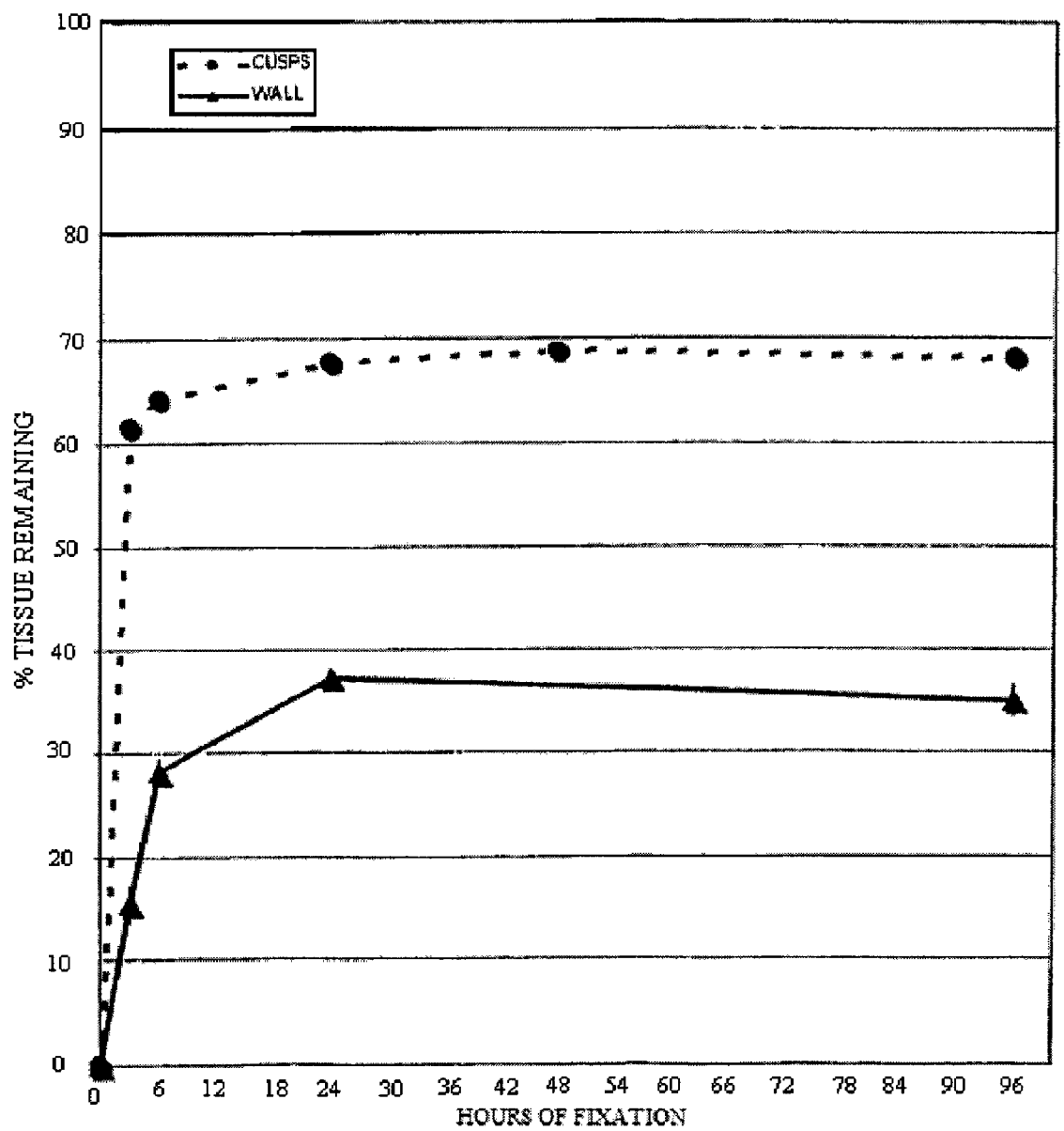
FIG. 3 is a graph which shows the resistance to digestion by proteolytic enzymes of wall tissue and of leaflets, relative to duration of fixation.

The leaflets (9 per condition) and coupons of aortic wall (12 per condition) were submitted to protease digestion at 50° C. for 24 hours according to the test described in J. Heart Valve Dis. 1996. The results are presented in FIG. 3 and indicate that maximum resistance to digestion of both cusps and aortic wall occurs after about 24 hours of cross linking.

c. Resistance to Digestion by Collagenase.

Figure 4:
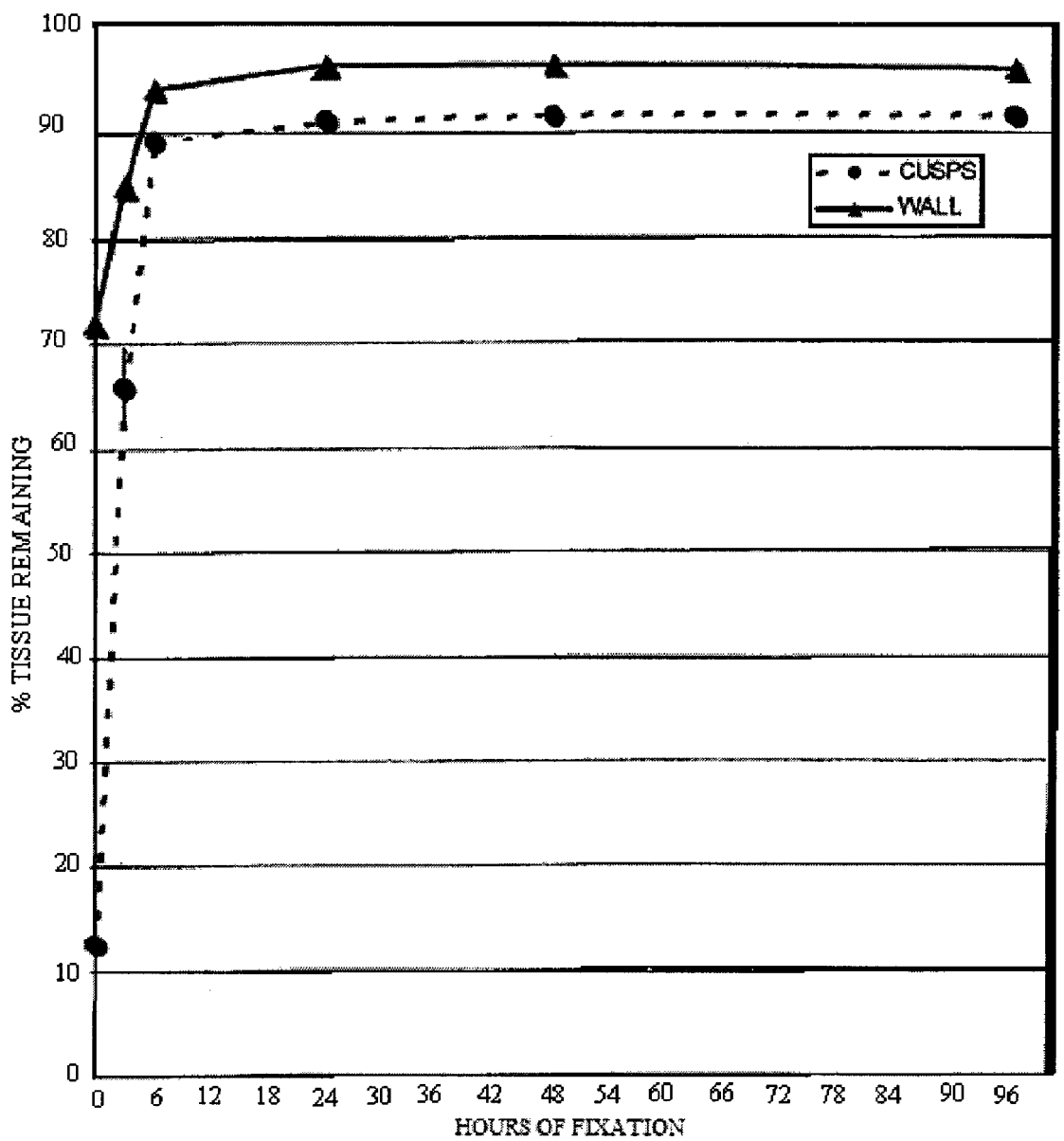
FIG. 4 is a graph which shows the resistance to digestion by collagenase of wall tissue and leaflets, relative to the duration of fixation.

The leaflets (9 per condition) and coupons of aortic wall (12 per condition) were submitted to collagenase digestion at 37° C. for 72 hours according to the test described in the above reference. The results shown in FIG. 4 demonstrate that maximum resistance is substantially obtained after approximately 24 hours of fixation and that resistance is only minimally improved as a result of treatment for another 24-hour period.

EXAMPLE 4

Following the good results obtained in Example 3, an experiment was carried out to compare tissue cross-linked using EDC and 112 mM DIA to standard glutaraldehyde-fixed tissue, generally using the same test regimens as in Example 3.

Porcine aortic roots were cross linked using an aqueous solution of 112 mM DIA, 20 mM HEPES buffer, pH 6.5, 20 mM EDC and 1 mM Sulfo-NHS. After 96 hours of incubation at room temperature, the valves were extensively washed with sterile saline to remove unreacted reagents and any reaction byproducts. The valves were sterilized 3 times according to the method of sterilization of Example 2, using 20% isopropanol. Standard glutaraldehyde-fixed and un-fixed porcine aortic roots were provided by Medtronic Heart Valves in Santa Ana, Calif. Leaflets and aortic wall coupons (5 mm.times.5 mm) were excised and submitted to the tests of cross linking as generally described in Example 3. In addition, leaflets and aortic wall coupons were implanted subdermally in young rats for 8 weeks to evaluate resistance to calcification.

a. Thermal Denaturation

The results of thermal denaturation of leaflets are presented in Table 4 A. The thermal denaturation temperature for fresh leaflets, (i.e. non-fixed leaflets) and glutaraldehyde-fixed leaflets were found to be 65.5° C. and 84.9° C., respectively, which is consistent with previous test results. The thermal denaturation temperature determined for EDC cross-linked leaflets is 80.5° C., which represents a significant increase of 15° C. over fresh tissue. Although slightly lower than glutaraldehyde-fixed leaflets, such is felt to be fully acceptable. This lower denaturation temperature along with the kinetic differences mentioned earlier indicate that EDC cross linking in the presence of 112 mM DIA induces different cross-links than those of glutaraldehyde-fixing.

TABLE 4 A

Denaturation Temperature
(° C., Mean +/− SEM)

| EDC cross linking (n = 6) | Glutaraldehyde-fixed (n = 6) | Fresh (n = 4) |
|---|---|---|
| 80.5 +/− 0.3 | 84.9 +/− 0.4 | 65.5 +/− 0.1 | b. Resistance to Protease Digestion

A slightly stronger than usual test solution was used for this test; 242 mg of pronase was dissolved in 250 ml of solution rather than only 150 mg. The results of resistance to protease digestion are presented in Table 4 B. Fresh tissue is completely digested after 24 hours of incubation. There is no significant difference between carbodiimide fixation using this high diamine concentration and standard glutaraldehyde cross linking for both cusps and aortic wall with respect to resistance to protease digestion. These results suggest that this cross linking method is as effective as glutaraldehyde-fixing.

TABLE 4 B

Resistance to Protease digestion
(% weight remaining, Mean +/− SEM)

| | EDC cross linking | Glutaraldehyde-fixed | Fresh |
|---|---|---|---|
| Cusps (n = 12) | 72.0 +/− 2.4 | 75.3 +/− 4.2 | 0 |
| Aortic wall (n = 12) | 28.0 +/− 0.8 | 26.3 +/− 2.1 | 0 |

The results of resistance to collagenase digestion are shown in Table 4 C. Fresh leaflets, composed mainly of collagen, are fully digested; however, a significant portion of each aortic wall remains. With respect to the cusps, there is no significant difference between EDC-fixed and the glutaraldehyde-fixed tissue; however, it seems that the glutaraldehyde-fixed wall tissue is slightly less resistant to collagenase digestion than the EDC-fixed tissue. Overall, the results show that tissue cross-linked with EDC and 112 mM DIA is at least as resistant to collagenase as is tissue cross-linked with glutaraldehyde.

TABLE 4 C

Resistance to Collagenase Digestion
(% weight remaining, Mean +/− SEM)

| | EDC cross linking | Glutaraldehyde-fixed | Fresh |
|---|---|---|---|
| Cusps (n = 12) | 94.6 +/− 5.6 | 97.6 +/− 5.7 | 0 |
| Aortic wall (n = 12) | 96.2 +/− 0.8 | 79.7 +/− 5.5 | 72.0 +/− 0.9 | c. Calcification after 8 Weeks Implantation in Young Rats.

Leaflets and wall coupons (1 cm×1 cm) were dissected from sterilized porcine aortic roots. The samples were washed 3 times for 2 minutes with sterile saline and then randomly implanted subdermally in young rats. After 8 weeks, the samples were retrieved, washed and submitted to quantitative calcium analysis as described in the above-mentioned reference.

TABLE 4 D

Calcification
($Ca^{++}$ mg/g of dry sample, Mean +/− SEM)

| | EDC cross linking | Glutaraldehyde-fixed |
|---|---|---|
| Cusps (n = 9) | 11.2 +/− 6.8 | 216.5 +/− 5.8 |
| Aortic wall (n = 9) | 39.9 +/− 2.6 | 82.1 +/− 4.6 |

The results presented in Table 4 D indicate that tissue cross-linked with EDC in the presence of 112 mM DIA, whether cusps or aortic walls, is very significantly more resistant to calcification than glutaraldehyde-fixed tissue.

Furthermore, aortic wall calcification was not only significantly lower than it was for glutaraldehyde-fixed aortic wall tissue, but it was also lower than comparable aortic wall tissue fixed as described in the '339 patent. The above-reported calcium level in wall tissue after 8 weeks of implantation is slightly below the levels previously seen after implantation for just 4 weeks. Previously after 8 weeks implantation, the calcium level in such aortic walls was around 80 mg $Ca^{++}$ per g of sample, which is a level substantially twice that now found in the present sample, and one that is considered to be clinically significant.

The results obtained in the foregoing examples show the effectiveness of the invention in minimizing the reduction in surface area that occurs as a result of a one-step fixation that has been carried out to improve the characteristics of bioprosthetic material, e.g. its thermal denaturation, its resistance to protease digestion, and its resistance to collagenase digestion. In this respect, for the last few decades, glutaraldehyde-fixing has been the generally accepted standard, and therefore comparison may fairly be made with glutaraldehyde-fixation of the same tissue. It has thus been shown that the characteristics of tissue treated using the improved fixation process compare favorably with the characteristics of the same tissue when treated with glutaraldehyde for 7 days in these three aspects. Example 3 also shows that it appears that the effects of fixation using this process are essentially maximized after incubation for about 24-48 hours and that further treatment, although not detrimental, may not be necessary. This 24-hour term of achieving ultimate cross linking can also be contrasted with other cross linking procedures which are substantially complete after an hour or 2 duration, indicating that different cross linking is very likely occurring, as the present process relies upon penetration deeply into fresh tissue over time. Therefore, although it can be seen that a very substantial improvement in properties is obtained after treatment for 8 hours, preferably the EDC-high amine concentration fixation is carried out at about room temperature for a period of at least 24 hours. Perhaps the most dramatic improvement occurs in the calcification resistance, which in many respects is one of the most important characteristics of a bioprosthetic device, inasmuch as calcification has been shown to be one of the primary causes of failure in prosthetic heart valves, resulting in stenosis and regurgitation in its operation. Although fixation by the process described in the '339 patent earlier resulted in some improvement in calcification resistance over comparable glutaraldehyde-fixed bioprosthetic tissue, Table 4 D shows that aortic wall tissue exhibits a resistance to calcification about twice that of glutaraldehyde-fixed tissue and that leaflets treated in this manner show a resistance nearly 20 times as great. This surprising calcification-resistance is expected to impart extremely valuable durability to bioprosthetic devices including tissue treated in accordance with this invention.

EXAMPLE 5

Variable Cross Linking of Pericardium Tissue

Tissue Preparation

Pericardium sheets are obtained from a slaughterhouse and rinsed extensively with ice cold saline until the rinse solution runs clear. The pericardium sheets are then cleaned to remove fat. The pericardium sheets are then cut into sheets, which are maintained on ice cold saline until ready for further processing.

The degree of desired crosslinking [fully cross linked (FX), partially cross linked (PX) or minimally cross linked (MX)] for the tissue is selected and the appropriate steps for the selected degree of cross linking are then followed, as described in detail below.

FX—Fixation

Each pericardium sheet is secured onto a template using holders and placed in a fixation container containing ice cold saline (S1 solution). When all the sheets are in the container, the container is covered and maintained at 0-4° C. The fixation solution, containing 112.5 MM 1,6-hexane diamine, 10 mM HEPES (pH 6.5), 20 mM EDC and 1 mM S—NHS. is then prepared. The saline solution is completely drained from the fixation container and immediately replaced with fixation solution, making sure that all the sheets are completely immersed in the fixation solution. The tissue is incubated for 96 hours at room temperature in the presence of the fixation solution.

At the end of fixation, the fixation solution is drained from each container and is completely removed from the sheets. Making sure that all sheets are kept wet throughout the process, the sheets are rinsed extensively with ice-cold saline solution (S1) until all reagents and by-products of the reactions are completely removed from the sheets. The fixed tissue is maintained IN S1 SOLUTION at 4° C. in a covered container until the next step.

FX—Sterilization

The fixed sheets are cut, if desired, to appropriate sizes, placed in individually labeled sterilization containers and immersed in saline (S1) to prevent drying. The fixation container is kept tightly covered until the next step. The sterilization solution, containing 10 mM HEPES, 0.65% NaCl, 20% isopropyl alcohol and 25 mM EDC, is prepared.

The saline solution is drained from the sterilization containers and is immediately replaced with sterilization solution, making sure that all the sheets are fully IMMERSED. The containers are covered tightly to prevent evaporation of the sterilization solution. The CONTAINERS ARE placed on a roller apparatus at 40±2° C. for 48±2 hours. After the sterilization time has been completed, the containers are removed from the incubator and stored at room temperature.

PX—Fixation

Each pericardium sheet is secured onto a template using holders and placed in a fixation container containing ice cold saline (S1 solution). When all the sheets are in the container, the container is covered and maintained at 0-4° C. The PX fixation solution, containing 112.5 mM 1,6-hexane diamine, 10 mM HEPES (pH 6.5), 2.5 mM EDC and 0.125 mM S—NHS, is then prepared.

The saline is then drained from each fixation container and immediately replaced with the PX fixation solution, making sure that all the sheets are completely immersed. The container is then covered and placed on a shaker, rotating at 100 rpm, for 96±2 hours. At the end of the fixation time, the fixation solution is drained from each container. Making sure that all sheets are kept wet throughout the process, the sheets are rinsed extensively with ice-cold saline solution (SI) until all reagents and by products have been completely removed from the tissue. The sheets are maintained at 4° C. in a covered container until the next step.

PX—Sterilization

Blocking—Treatment with TRIS/ethanolamine Blocking Reagent

The blocking solution, containing 100 mM Tris, 100 mM ethanolamine, 20% isopropyl alcohol and 20 mM EDC, is prepared. The saline solution is drained from the container and immediately replaced with the blocking solution, making sure to completely cover all the sheets. The container is then placed in an incubator at 40±2° C. for 48±2 hours. At the end of the blocking period, the container is removed from the incubator and brought to room temperature, after which the blocking solution is drained from the container. Making sure that all sheets are kept wet throughout process, the sheets are rinsed with ice-cold saline solution until all reagents and by-products are completely removed. The sheets are then placed in individual sterilization containers and covered with ice-cold saline solution until the next step.

Final Sterlization—Treatment with EDC under Sterilizing Conditions

The final sterilization solution, containing 20% isopropanol 20 mM EDC and 10 mM HEPES, is prepared. The saline is then drained from the sterilization containers and immediately replaced with the final sterilization solution, making sure to cover all sheets completely. The containers are then covered tightly and placed on a roller apparatus in an incubator at 40±2° C. for 48±2 hours. After the reaction time is complete, the containers are removed from the incubator and then stored at room temperature.

MX—Blocking

Each sheet is secured onto a template using holders, placed in a fixation container and immersed completely in saline solution (S1). The container is then covered and maintained at 4° C. while preparing the sterilization solution. The blocking solution, containing 20% isopropanol, 100 mM TRIS, 100 mM ethanoloamine, and 20 mM EDC, is then prepared.

The saline solution is then drained from the fixation container and immediately replaced with the blocking solution, making sure to cover each sheet completely with the blocking solution. The container is then covered tightly to prevent evaporation and placed in an incubator at 40±2° C. for 48± hours. At the end of the incubation period, the container is removed from the incubator and brought to room temperature. Making sure that all the sheets remain wet throughout the process, the sheets are then rinsed thoroughly with saline solution (S1) until all reagents and by-products have been removed from the sheets. The sheets are then placed in individually labeled sterilization containers and completely immersed in saline (S1) to prevent drying.

MX Final Sterilization

The final sterilization solution, containing 20% isopropanol, 10 mM HEPES, 0.65% NaCl, and 20 mM EDC, is then prepared. The saline is then drained from the sterilization containers and immediately replaced with the final sterilization solution, making sure that all the sheets are completely immersed in the sterilization solution. The sterilization containers are then covered tightly to prevent evaporation and placed in an incubator on a roller apparatus at 40±2° C. for 48±2 hours. At the end of the incubation period, the containers are removed from the incubator and brought to room temperature. The containers are then stored at room temperature.

EXAMPLE 6

Determination of Cross Linking

MX, PX and FX tissues obtained by the method set forth in Example 5 were subjected to shrinkage temperature and pronase digestion testing in order to determine the degree of cross linking obtained with the procedure outlined above. The temperature of protein denaturation (heat shrinkage) is a well-accepted method of measuring the cross linking of collagen-based tissue. See, Sung et al., J. Biomed. Mater. Res. 1997; Billiar et al., J. Biomed. Mater. Res. 2001; U.S. Pat. No. 5,447,536. Resistance to proteolysis is likewise a well-accepted method for characterizing cross linking. Sung et al., 1997; Billiar et al., 2001; U.S. Pat. No. 5,447,536; Girardot, J. M. et al., J. Heart Valve Dis., 5(5), 518-25, (1996).

The shrink temperature is determined by an art recognized method. Sung et al., 1997; Billiar et al., 2001; U.S. Pat. No. 5,447,536. Essentially, a sample is secured between two clamps in a water bath. The water bath is heated gradually until a continuous and appreciable movement is seen on a scale adapted to measure movement of one of the clamps (the so-called pivot clamp). The temperature at which such movement begins is designated the shrink temperature. The lower the shrink temperature, the less the degree of cross linking.

Samples (8 samples, about 2 mm×2 cm each) were cut from 9 different lots of processed equine pericardium that had been subjected to MX, PX and FX processing according to Example 5, above. One end of each sample was put in a fixed clamp on a heat shrink apparatus and the other end was clipped into a pivot clamp on the same apparatus that was equipped with a pointer designed to show movement of the pivot clamp. The water bath was headed, thereby heating the tissue, with stirring of the water bath. The probe of a digital thermometer was placed at the same level as the sample clamps. The water temperature was started at 55-60° C. and ramped upward at approximately 0.1° C./sec. When the needle from the pivot clamp registered a constant and appreciable movement (>2 mm) the temperature was recorded. Water was changed between runs and the next sample was measured by the same procedure. The shrinkage temperatures for MX, PX and FX samples produced by the process set forth in Example 5, above, and tested according to this procedure are set forth in Table 5, below.

The enzyme digestion test uses pronase, a non-specific proteolytic enzyme, to digest non-cross linked protein. Tissue samples are rinsed and incubated in an enzyme solution for a specified period of time. The mass of the dried tissue sample is taken before and after digestion to give a ratio of undigested protein. The degree of digestion is inversely related to the degree of cross linking.

Samples (5, each about 1 cm×1 cm) were cut from 10 different lots of MX, PX and FX processed equine pericardium that were obtained by the procedures outlined in Example 5, above. The samples were washed 3 times in aqueous 0.9% NaCl (two 5 minute rinses and one 15 minute rinse). The samples were left to air dry overnight in a tissue culture hood. Samples were weighed on an analytical balance the next day and weights ($W_{initial}$) were recorded.

Aqueous HEPES buffer was prepared fresh on the day of enzyme digestion test. Protease and $CaCl_2$ were added at 1 mg/ml and 0.6 mg/ml, respectively, to the buffer shortly before it was added to the tissue samples. Enzyme solution (3 ml) was added to each sample. The samples were incubated at 50° C. with shaking for 24 hours. After incubation, the samples were removed from the enzyme, blotted dry 3 times on a non-linting tissue and left to dry overnight in the tissue culture hood. Final masses of the samples were measured ($W_{final}$) and a simple ratio of digested to undigested tissue weight was calculated using the following formula: 100%× ($W_{final}/W_{initial}$), wherein $W_{final}$ is the dry weight of digested tissue and $W_{initial}$ is the dry weight of the undigested tissue. The results for MX, PX and FX tissues made by the process set forth in Example 5, above, appear in Table 5, below.

As can be seen in Table 5, below, the process of the present invention provides a range of cross linking ranging from minimally cross linked to partially cross linked to fully cross linked.

TABLE 5

| Degree of Cross Linking | Fixation | Intermediate Sterilization | Final Sterilization | Shrinkage Temperature | Pronase Digestion (% Tissue Remaining) |
| --- | --- | --- | --- | --- | --- |
| FX | 20 mM EDC 1 mM S-NHS 112.5 mM 1,6-hexane diamine 10 mM HEPES (pH 6.5) | None | 20% Isopropanol 25 mM EDC 10 mM HEPES | ~80° C. | ~88% |
| PX | 2.5 mM EDC 0.125 mM S-NHS 112.5 mM 1,6-hexane diamine 10 mM HEPES (pH 6.5) | 20% Isopropanol 20 mM g EDC 10 mM HEPES | 20% Isopropanol 25 mM EDC 10 mM HEPES | ~73° C. | ~72% |
| MX | None | 20% Isopropanol 20 mM EDC 100 mM TRIS 100 mM ethanolamine | 20% Isopropanol 20 mM EDC 10 mM HEPES | ~68° C. | ~26% |

Although the invention has been set forth with respect to certain preferred embodiments which constitute the best mode presently known to the inventors for carrying out the invention, it should be understood that various changes and modifications that would be obvious to one having ordinary skill in this art may be made without departing from the scope of the invention which is defined in the claims appended hereto. For example, although treatment is preferably carried out using an aqueous solution, other biocompatible solvents, or combinations of solvents, might instead be used as generally known in this art.

Particular features of the invention are emphasized in the claims which follow.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of making sterilized and partially cross linked biological tissue from fresh tissue, which method comprises the steps of: a) contacting fresh biological tissue with a cross linking solution containing a cross linking agent, from 1 to 5 mM of a coupling agent and a low concentration of a coupling enhancer to produce partially cross linked tissue, b) contacting the partially cross linked tissue with a blocking solution that comprises a monoamine blocking agent and a sterilizing agent; and c) then contacting said tissue with a final sterilizing solution that comprises a sterilizing agent and no blocking agent to produce the sterilized and partially cross linked biological tissue, which tissue has such a degree of cross linking that it resists enzymatic degradation to an extent that is statistically significantly less than fully cross linked tissue and statistically significantly greater than minimally cross linked tissue.

2. The method of claim 1 wherein the cross linking agent is an alkane diamine, the coupling agent is a carbodiimide, and the coupling enhancer is N-hydroxysuccinimide (NHS) or N-hydroxysulfosuccinimide (S-NHS).

3. The method of claim 2 wherein the alkane diamine is hexane diamine, the coupling agent is 1-ethyl-3-dimethylaminopropylcarbodiimide (EDC) and the coupling enhancer is S-NHS.

4. The method of claim 1 wherein the coupling enhancer has a concentration in a range of about 0.05 to about 0.4 mM.

5. The method of claim 3 wherein the coupling agent is EDC having a concentration of from about 1 to about 2.5 mM.

6. The method of claim 5 wherein the coupling enhancer has a concentration of about 0.005 to about 0.125 mM.

7. The method of claim 1 wherein the blocking solution further comprises a penetration enhancer.

8. The method of claim 7 wherein the penetration enhancer is a lower alkanol.

9. The method of claim 8 wherein the lower alkanol is selected from methanol, ethanol, n-propanol, i-propanol, t-butanol, i-butanol, n-butanol and s-butanol.

10. The method of claim 8 wherein the lower alkanol is isopropanol.

11. The method of claim 1 wherein said blocking agent in the blocking solution is a monoamine in a concentration of from about 50 to about 250 mM.

12. The method of claim 11 wherein the monoamine is an alcohol amine.

13. The method of claim 12 wherein the alcohol amine is ethanolamine.

14. The method of claim 11 wherein the blocking solution further comprises a buffer.

15. The method of claim 14 wherein said buffer is an organic amine.

16. The method of claim 15 wherein the organic amine is tris-(hydroxymethyl)aminomethane buffer.

17. The method of claim 1 wherein the blocking solution comprises EDC as the sterilizing agent.

18. The method of claim 1 wherein at the end of step b), the tissue is rinsed to remove all reagents and byproducts.

19. A method of making sterilized and partially cross linked biological tissue from fresh tissue which method comprises the steps of: a) contacting fresh biological tissue with a cross linking solution containing a cross linking agent, from 0.1 to 5 mM of a coupling agent and from 0.1 to 0.4 mM of a coupling enhancer to produce partially cross linked tissue, b) contacting the partially cross linked tissue with a blocking solution that comprises a monoamine blocking agent, a penetration enhancer and a sterilizing agent; and c) then contacting said tissue with a final sterilizing solution which final sterilizing solution comprises a sterilizing agent and no blocking agent to produce sterilized and partially cross linked biological tissue, which partially cross linked tissue when treated with 1 mg/ml of pronase for 24 hours at about 50° C. results in more than 50% but less than 80% tissue remaining 20. The method of claim 19 wherein the cross linking agent is an alkane diamine, the coupling agent is a carbodiimide, and the coupling enhancer is N-hydroxysuccinimide (NHS) or N-hydroxysulfosuccinimide (S-NHS).

21. The method of claim 20 wherein the blocking solution comprises about 50 to about 250 mM of the monoamine and about 10 to about 25% of a C1-C8alkanol as the penetration enhancer.

22. The method of claim 19 wherein the final sterilization solution consists essentially of 1-ethyl-3-dimethylaminopropylcarbodiimide (EDC), an alkanol and a buffer.

23. The method of claim 22 wherein the final sterilization solution comprises N-2-hydroxyethylpiperazine -N'-ethanesulfonic acid (HEPES) as a buffer.

24. The method of claim 19 wherein at the end of step b), the tissue is rinsed to remove all reagents and byproducts.

25. A method of making a sterilized and partially cross linked biological tissue from fresh tissue, which method comprises the steps of: a) contacting fresh biological tissue with a cross linking solution containing a cross linking agent, concentration of a carbodiimide coupling agent between about 1 and about 2.5 mM and a concentration of between 0.05 and 0.4 mM of a coupling enhancer to produce partially cross linked tissue, b) contacting the partially cross linked tissue with a blocking solution that comprises a monoamine blocking agent, and with a carbodiimide sterilizing agent in the presence of a penetration enhancer and c) then contacting said tissue with a final sterilizing solution which comprises a carbodiimide sterilizing agent and no blocking agent to produce sterilized and partially cross linked biological tissue, which tissue has a shrinkage temperature at least 4° C. above that of the fresh tissue and at least 6° C. below fully cross linked tissue.

26. The method of claim 25 wherein the cross linking agent is an alkane diamine, the coupling agent is 1-ethyl-3-dimethylaminopropylcarbodiimide (EDC), and the coupling enhancer is N-hydroxysuccinimide (NHS) or N-hydroxysulfosuccinimide (S-NHS).

27. The method of claim 25 wherein a concentration of EDC of about 2.5 mM is used in the cross linking solution.

28. The method of claim 25 wherein step b) employs about 50 to 250 mM of the monoamine blocking agent and about 10 to about 25% of a C1-C8 alkanol as the penetration enhancer.

29. The method of claim 25 wherein at the end of step b), the tissue is rinsed to remove all reagents and byproducts.

30. The method of claim 25 wherein the final sterilization solution comprises N-2-hydroxyethylpiperazine N'-ethanesulfonic acid (HEPES) as a buffer.

31. The method of claim 25 wherein the final sterilization solution consists essentially of EDC, an alkanol and a buffer.

* * * * *

UNITED STATES PATENT AND TRADEMARK OFFICE
CERTIFICATE OF CORRECTION

Page 1 of 1

PATENT NO. : 7,918,899 B2
APPLICATION NO. : 11/276398
DATED : April 5, 2011
INVENTOR(S) : Girardot et al.

It is certified that error appears in the above-identified patent and that said Letters Patent is hereby corrected as shown below:

Column 24, Line 22, Claim 19; delete "0.1" and insert --0.01-- therefor.

Column 24, Line 32, Claim 19; insert a --.-- at the end of line 32.

Column 24, Line 52, Claim 25; after "agent," insert --a low--.

Signed and Sealed this
Seventh Day of June, 2011

David J. Kappos
*Director of the United States Patent and Trademark Office*